United States Patent
Divi et al.

(10) Patent No.: US 9,447,024 B1
(45) Date of Patent: Sep. 20, 2016

(54) PROCESS FOR THE PREPARATION OF LACOSAMIDE

(71) Applicant: Divi's Laboratories Limited, Ameerpet, Hyderabad (IN)

(72) Inventors: Satchandra Kiran Divi, Hyderabad (IN); Mysore Aswatha Narayana Rao, Hyderabad (IN); Shaik Nowshuddin, Hyderabad (IN)

(73) Assignee: Divi's Laboratories Limited (IN)

( * ) Notice: Subject to any disclaimer, the term of this patent is extended or adjusted under 35 U.S.C. 154(b) by 0 days.

(21) Appl. No.: 14/885,321

(22) Filed: Oct. 16, 2015

(30) Foreign Application Priority Data

Sep. 18, 2015 (IN) .......................... 5001/CHE/2015

(51) Int. Cl.
 *C07C 231/14* (2006.01)
(52) U.S. Cl.
 CPC .................................. *C07C 231/14* (2013.01)
(58) Field of Classification Search
 CPC .................................................. C07C 231/14
 See application file for complete search history.

(56) References Cited

U.S. PATENT DOCUMENTS

| | | |
|---|---|---|
| 5,773,475 A | 6/1998 | Kohn |
| 8,093,426 B2 | 1/2012 | Madhra et al. |
| 8,378,142 B2 | 2/2013 | Madhra et al. |
| 8,598,386 B2 | 12/2013 | Wisdom et al. |
| 8,796,488 B2 | 8/2014 | Bologna et al. |
| 8,853,439 B2 | 10/2014 | Pandey et al. |
| 2012/0095251 A1* | 4/2012 | Wisdom ................ C07C 231/12 560/29 |
| 2014/0018577 A1 | 1/2014 | Merschaert et al. |

FOREIGN PATENT DOCUMENTS

WO   WO 2011/092559   *  8/2011

OTHER PUBLICATIONS

Salome, et al, Synthesis and Anticonvulsant Activities of N-(4'-Substituted)benzyl(r)-2-Acetamido-3-methoxypropionamides, J. Medicinal Chemistry, 2010, 53, 1288-1305, Supporting Information, S-101.
Choi, et al., Synthesis and Anticonvulsant Activities of N-Benzyl-2-acetamidopropionamide Derivatives, Journal of Medicinal Chemistry, 1996, 39,1907-1916.
Ilieva, et al., Computational Study of the Aminolysis of Esters. The Reaction of Methylformate with Ammonia, J. Organic Chemistry, 2003, 68, 1496-1502.

* cited by examiner

*Primary Examiner* — Shailendra Kumar
(74) *Attorney, Agent, or Firm* — Caesar Rivise, PC

(57) ABSTRACT

A novel process for the preparation of (R)-2-acetamido-N-benzyl-3-methoxypropionamide (Lacosamide) is described. It comprises reacting N-acetyl-D-serine methyl ester with benzylamine catalyzed by a non-nucleophilic base to obtain (R)-2-acetamido-2-N-benzyl-3-hydroxy propionamide followed by its methylation.

4 Claims, No Drawings

PROCESS FOR THE PREPARATION OF LACOSAMIDE

FIELD OF INVENTION

The present invention relates to an improved process for the preparation of (R)-2-acetamido-N-benzyl-3-methoxypropionamide, known as Lacosamide.

BACKGROUND OF THE INVENTION

Lacosamide is a chiral molecule useful in treating convulsions and pain. It was approved by USFDA in 2008 and is marketed by UCB under the trade name VIMPAT®. It is chemically (R)-2-acetamido-N-benzyl-3-methoxypropionamide (formula I) having the following structure:

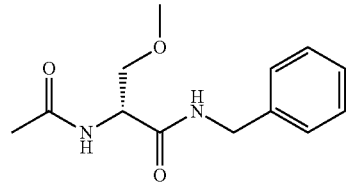

(I)

The U.S. Pat. No. 5,773,475 describes three schemes for the preparation of Lacosamide. Scheme-1 involves conversion of D-serine to its methyl ester hydrochloride followed by amidation with benzylamine. Acetylation of the benzylamide followed by Williamson etherification resulted in Lacosamide.

In this scheme, the benzylamide intermediate is obtained with poor chiral purity due to racemization. Also, methylation stage involves the use of methyl iodide, which is a low boiling, hazardous reagent, and silver oxide, which is expensive. The scheme-2 involves acetylation of D-serine followed by coupling with benzylamine using mixed anhydride method and finally O-methylation using methyl iodide and silver oxide.

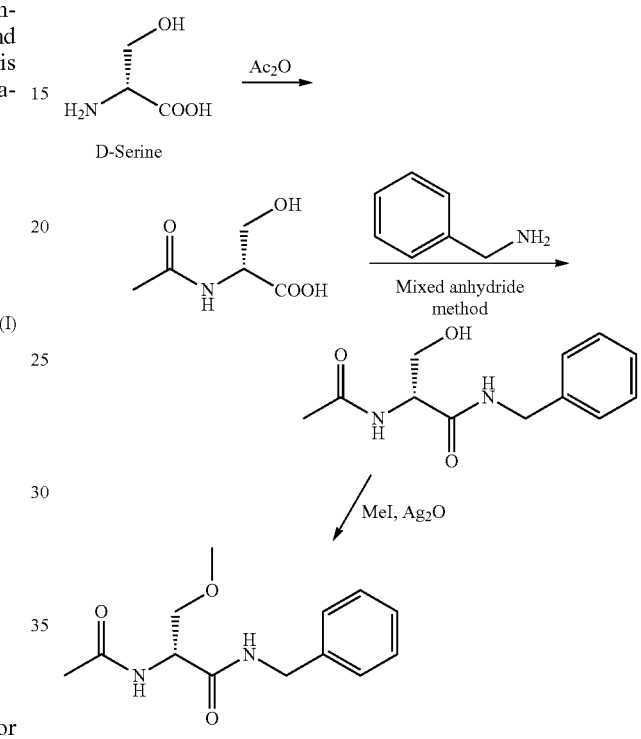

The third method (Scheme-3) involves protection of the amino group of D-serine with benzyloxycarbonyl (Cbz), followed by methylation. This is followed by hydrolysis, benzyl amidation, Cbz-deprotection and N-acetylation.

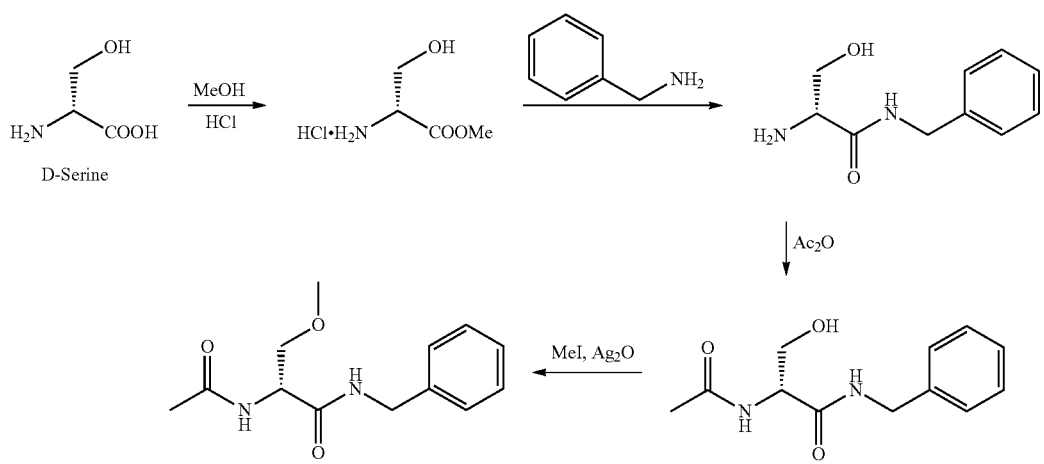

Scheme-3

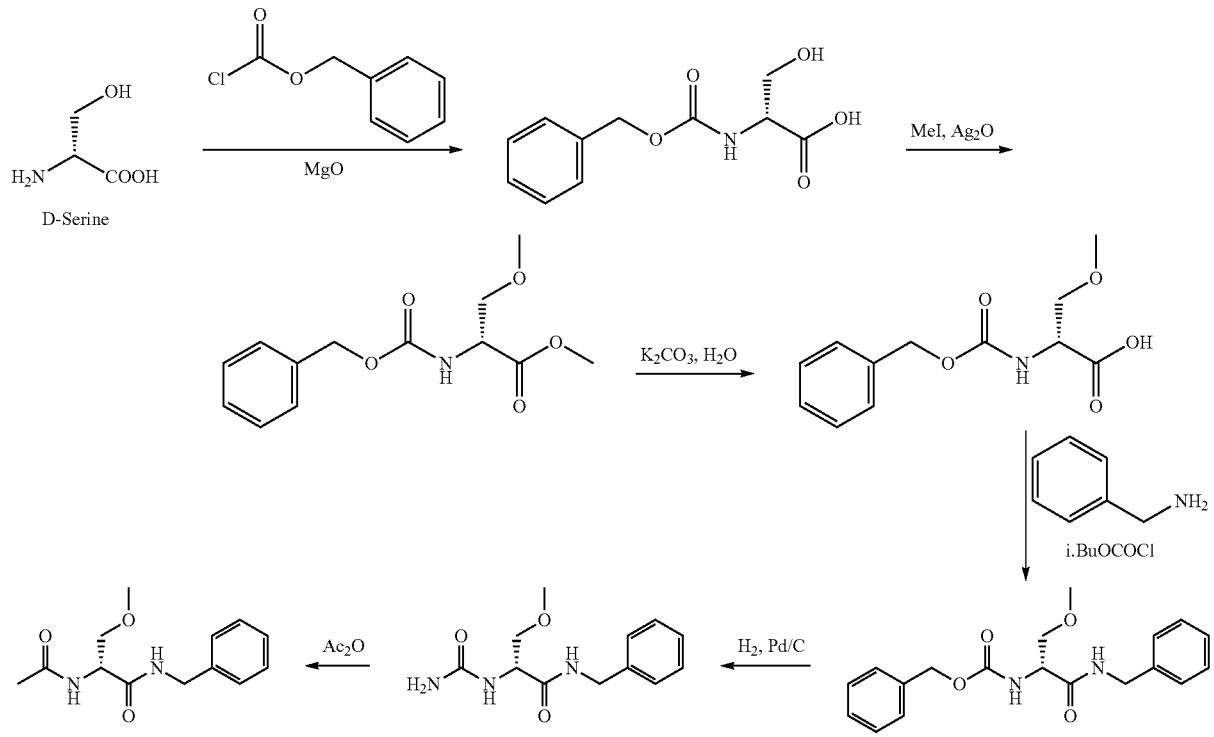

The Scheme-3 is complicated as it consists of a large number of steps. It involves protection and deprotection of the amino group. In addition, the methylation step results in two methylations, methylation of alcoholic group and esterification of the carboxylic group, requiring hydrolysis of the ester before coupling with benzylamine.

Later UCB patent, U.S. Pat. No. 7,884,134, described a process involving N-Boc-D-serine and methylation using a phase-transfer catalyst. Another modification described is the use of butyllithium/dimethyl sulfate as the methylating agent. Ranbaxy laboratories reported a process (U.S. Pat. No. 8,093,426) wherein a trityl moiety was used as bulky protecting group to minimize nucleophilic attack on the chiral carbon to suppress racemization. A divisional patent, U.S. Pat. No. 8,378,142, claimed the trityl intermediate, N-benzyl-O-methyl-$N^2$-trityl-D-serinamide.

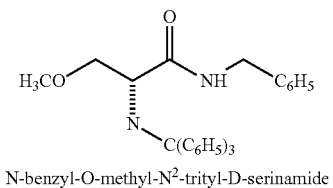

N-benzyl-O-methyl-$N^2$-trityl-D-serinamide

U.S. Pat. No. 8,853,439 describes a process which involves protecting both amino and alcoholic groups of D-serine (Scheme-4).

Scheme-4

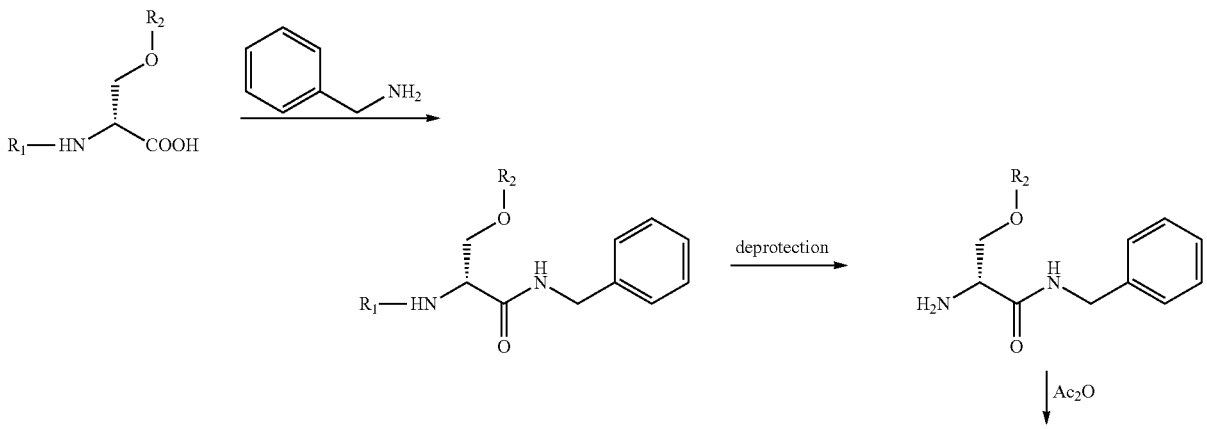

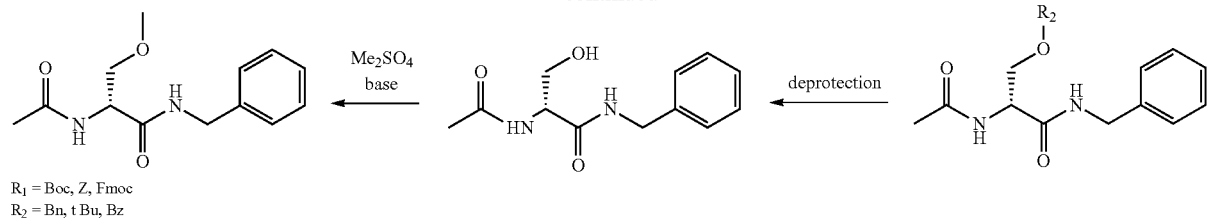

R₁ = Boc, Z, Fmoc
R₂ = Bn, t Bu, Bz

U.S. Pat. No. 8,598,386 describes a process which involves condensation of Boc-D-serine with benzylamine using 2,4,6-tripropyl-2,4,6-trioxo-1,3,5,2,4,6-trioxatriphosphorinane (T3P®) as a coupling agent (Scheme-5).

Scheme-5

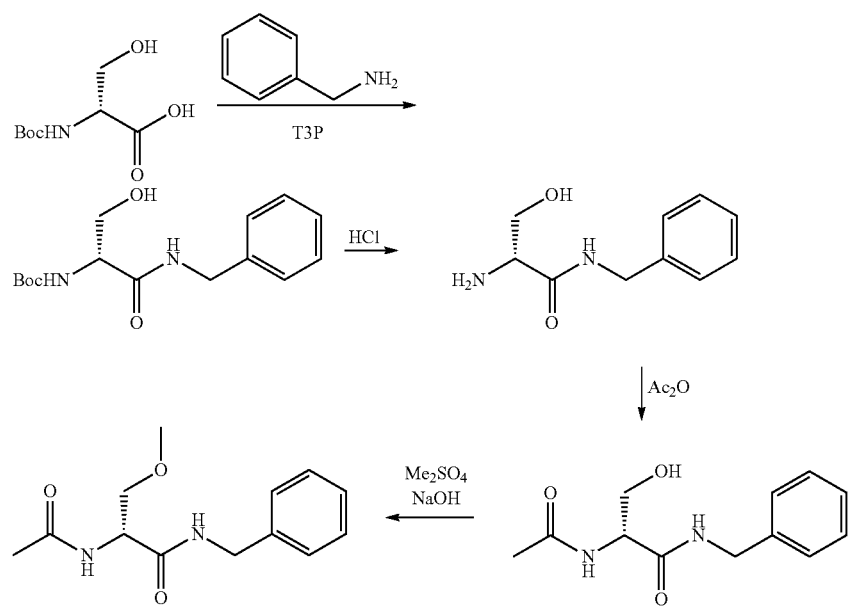

While all the above methods started from D-serine as the starting material, the U.S. Pat. No. 8,796,488 describes a process from (DL)-serine involving final resolution using 2-(S)-chloro mandelic acid (Scheme-6).

Scheme-6

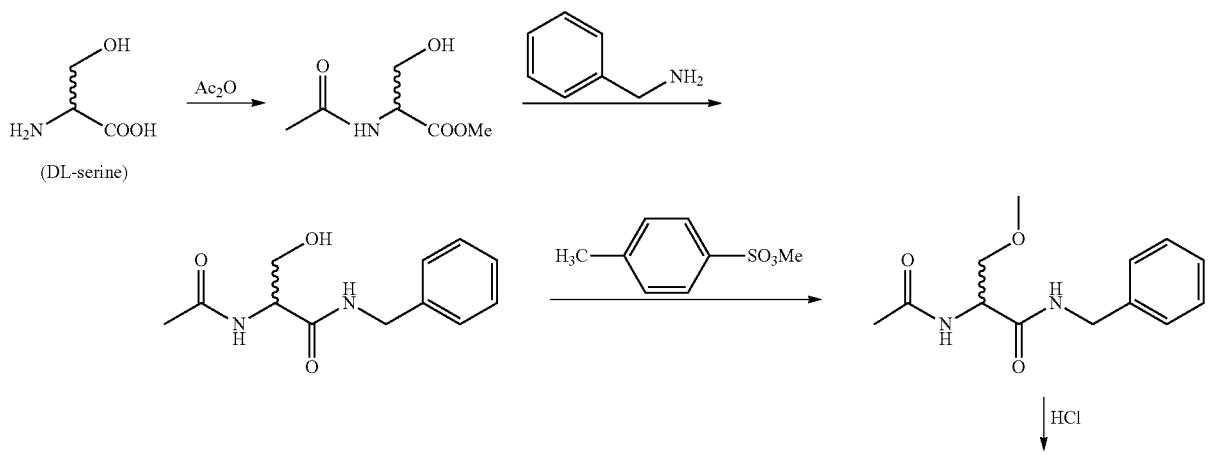

-continued

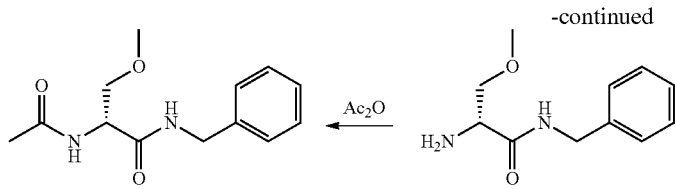

A new application from UCB, US 2014/0018577 describes a process via resolution of O-methyl-DL-serine using a chiral acid or through enzyme, followed by acetylation and condensation with benzylamine after activation using alkyl chloroformate (Scheme-7).

Scheme-7

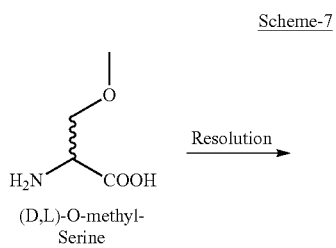

(D,L)-O-methyl-Serine

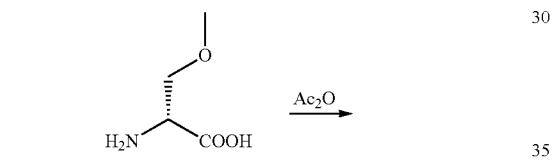

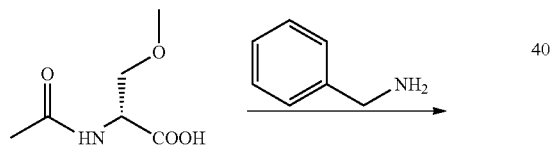

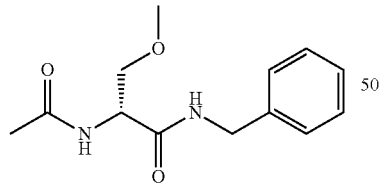

The starting compound, O-methyl-DL-serine is a special chemical and cannot be prepared easily from DL-serine. Apart from using expensive resolving agents or enzymes for resolution, the final step of condensation with benzylamine using isobutylchloroformate requires very low temperature (−20 to −10° C.). The methods based on (DL)-serine involve several steps and are expensive even if the unwanted isomer is recovered.

Because of the enumerated drawbacks of the above-mentioned processes, there is a need for developing an improved process.

SUMMARY OF THE INVENTION

The present invention provides a novel process for the preparation of Lacosamide of formula I

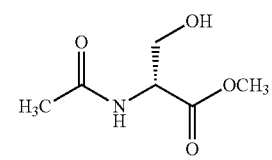

(I)

comprising the steps of
(a) reacting N-acetyl-D-serine methyl ester of formula II

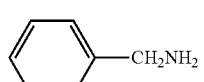

(II)

with benzylamine of formula (III)

(III)

$\text{C}_6\text{H}_5\text{-CH}_2\text{NH}_2$ in the presence of a non-nucleophilic base, to produce (R)-2-acetamido-N-benzyl-3-hydroxypropionamide of formula IV; and

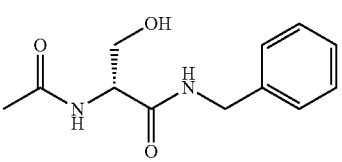

(IV)

(b) methylation of (IV) to obtain Lacosamide of formula I.

DETAILED DESCRIPTION OF THE INVENTION

The present invention provides a novel process for the preparation of Lacosamide of formula I comprising the steps of (a) reacting N-acetyl-D-serine methyl ester of formula II

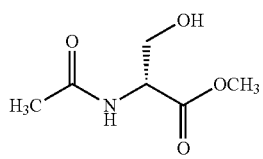
(II)

with benzylamine of formula (III)

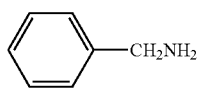
(III)

in the presence of a non-nucleophilic base to produce (R)-2-acetamido-N-benzyl-3-hydroxypropionamide of formula IV; and

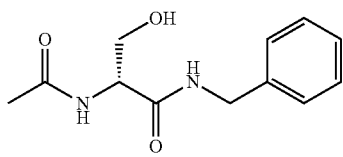
(IV)

(b) methylation of (IV) to obtain lacosamide of formula I.

The required starting material, N-acetyl-D-serine methyl ester of formula II, can be prepared by the methods described in the literature (*J. Medicinal Chemistry*, 2010, 53, 1288-1305, *Supporting information, S*-101).

Choi et al, (Journal of Medicinal Chemistry, 1996, 39, 1907-1916) had described significant racemization during the preparation of D-serine benzylamide (Scheme-8).

Scheme-8

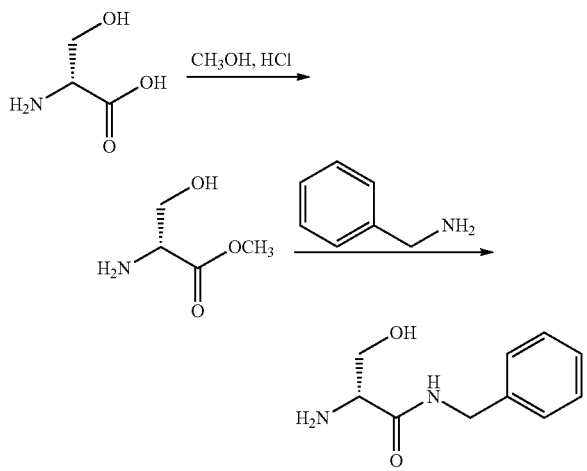

Reacting D-serine with methanol containing HCl, under reflux for 18 hours, followed by heating with four equivalents of benzylamine for another 18 hours resulted in the benzylamide in 27% yield, which was found to be a 2:1 mixture of enantiomers. To overcome the racemization problem, Choi et al modified their process by first acetylating D-serine with acetic anhydride followed by condensing with benzylamine using isobutylchloroformate and N-methyl morpholine (NMM), at −78° C. to obtain (IV) in 38% yields, after flash column chromatography on SiO$_2$ gel. Here, although no racemization was observed, the process is not suitable at industrial scale as it requires very low temperature (−78° C.) and isolation of the product by column chromatography, besides poor yield (36%).

Since the nucleophilicity of the free amino group may trigger racemization, masking the amino group may help in reducing racemization. We therefore envisaged that N-acetyl-D-serine methyl ester (II) maybe a better substrate. Thus, when (II) is treated with two equivalents of benzylamine (III) at room temperature, (IV) is obtained in 83% yield and 96% chiral purity. It is to be noted that the temperature plays an important role. At higher temperature, both yield and chiral purity are decreased. For example, at 60° C. for 12 hours, (IV) is obtained in 75% yield with only 78% chiral purity.

The U.S. Pat. No. 8,796,488 describes a process for Lacosamide (Scheme-6) using a similar reaction, where the resumes N-acetyl-D,L-serine methyl ester is heated at 65° C. with 5 equivalents of benzylamine to obtain N-acetyl-D,L-serine benzylamide in 84% yield. At such a temperature, significant racemization should take place. The chiral purity of the product was of no consequence because the authors used racemic starting material. The authors achieved the required chiral purity through resolution using 2-(S)-chloro mandelic acid, an expensive resolving agent. Furthermore, the process is complicated by the fact that the acetyl group is removed to free the amino group to facilitate resolution with a chiral acid. The required acetyl group is again introduced at the final step.

The present invention has overcome these steps. During the optimization experiments of the present invention, the mole equivalents of benzylamine were varied. At 1.5 equivalents of benzylamine, which is the minimum amount required to carry out the reaction without any other solvent, the yields were low (22%) and the reaction was incomplete. Two equivalents are optimum and at 3 or 5 equivalents no improvement in the yields and purity were observed.

The kinetics of an analogous reaction of methyl formate ester with ammonia to give an amide has been investigated through computational studies (Ilieva. S. et al, *J. Organic Chemistry*, 2003, 68, 1496-1502). The study showed that a mechanism involving a second molecule of ammonia catalyzing the reaction is energetically favored, over a non-catalyzed mechanism based on the fact that the activation energy for a reaction catalyzed by a second molecule of ammonia is lower than that of un-catalyzed reaction. We also observed in the present study, two equivalents of benzylamine are required for the reaction to be completed. We reasoned that, while one molecule is required as reactant, a second molecule is required for catalyzing the reaction. Since benzylamine is a weak base, we further reasoned that a stronger non-nucleophilic base should be able to catalyze the reaction in a better manner.

It was gratifying to note that addition of catalytic amount of triethylamine as a non-nucleophilic base, indeed improved the reaction to a significant extent. Addition of 0.2 equivalent of triethylamine to the reaction resulted in obtaining the product in 93% yield, compared to only 82% without triethylamine. The chiral purity also improved from 96.2% to >98.5%. Here also, temperature plays an important role. Room temperature, about 25° C., is optimum. At 60° C. the yield decreases to 69% and chiral purity is only 81%. At 40° C. the yield is 82% with 92% chiral purity.

Other non-nucleophilic bases such as diisopropylethyl amine (DIPEA), N-methyl morpholine (NMM), 1,4-diazabicyclo-[2.2.2]octane (DABCO) and 1,8-diazabicyclo[5.4.0]undec-7-ene (DBU) may also be used. All the non-nucleophilic bases studied gave product of >98% chiral purity. However, the yields were lower.

Thus the present invention process for (IV) is simple, economical and industrially useful.

In the next stage, methylation of the compound (IV) produces Lacosamide (I). Although several methylating agents such as methyl iodide, diazomethane, methyl arylsulfonate, methylalkyl sulfonate or trimethyl phosphonate may be used, dimethyl sulfate is preferred because it is inexpensive, easily available and highly reactive. The methylation of the compound (IV) is carried out in a suitable solvent such as acetonitrile, tetrahydrofuran or dimethylformamide in the presence of a base, such as sodium hydroxide dissolved in minimum amount of water. The reaction is best conducted at room temperature and will be completed in 1 to 2 hours. After usual work up and recrystallization from acetone and diisopropyl ether, Lacosamide is obtained in good yield and purity.

The embodiments of the present invention are illustrated in the following examples, which are not intended in any way to limit the scope of the invention. One skilled in the art can modify the details to suit the inputs and desired outcomes without affecting the present invention.

EXAMPLES

Chemical purity was determined using HPLC under the following conditions:
Column: BDS Hypersil C18, 250×4.6 mm, 5 μm
Mobile phase: Water: Acetonitrile (80:20); flow rate: 1.0 ml/min
Column Temperature: 30° C.
Detection: 210 nm
Enantiomeric purity was determined using HPLC under the following conditions:
Column: Chiralcel AD-H, 150×4.6 mm, 5μ
Mobile phase: n-Hexane: Ethanol: TFA (60:40:0.1), flow rate: 0.5 ml/min
Column Temperature: 27° C.
Detection: 210 nm Example-1

Preparation of D-Serine Methyl Ester Hydrochloride

D-serine (100 g, 0.9515 mole) was suspended in 600 ml methanol at room temperature. Acetyl chloride (224.0 g, 2.8545 mole) was added drop wise at −5° C. to 0° C. and stirred for 30 minutes. The reaction mixture was refluxed for 15 hours. Evaporation of the reaction mixture under reduced pressure followed by crystallization of the resulting residue from methanol and methyl tert-butyl ether, resulted in colorless solid of D-serine methyl ester hydrochloride (134.7 g, Yield: 91%, HPLC: 99.6%)

M.R: 165–167° C. (Lit.: 163–165° C., *Tetrahedron Letters*, 2012, 53, 1668-1670,)[α]$_D^{20}$=3.7 (C=4 in EtOH); IR(KBr): 3361, 2921, 2660, 2732, 2550, 2488, 2134, 2079, 1922, 1747, 1592, 1505, 1471, 1444, 1431, 1382, 1343, 1297, 1258, 1187, 1158, 1128, 1094, 1038, 969, 900, 793, 844, 580, 469 Cm$^{-1}$; H$^1$NMR: (300 MHz, DMSO), δ3.745 (s, 3H), 3.82 (s, 2H), 4.11 (s, 1H), 5.63 (s, 1H), 8.58 (s, 2H); $^{13}$CNMR: (300 MHz, DMSO), δ 52.66, 54.37, 59.38, 161.39.

Example-2

Preparation of N-Acetyl-D-Serine Methyl Ester

D-Serine methyl ester hydrochloride (100 g, 0.6430 mole) was suspended in 500 ml dichloromethane. To this was added triethylamine (136.6 g, 1.35 mole) at 0-5° C., followed by acetyl chloride (53.06 g, 0.6751 mole) drop wise at −10° C. The reaction mixture was stirred at −10° C. for 3 hours, filtered to remove salts and the filtrate was evaporated. The resulting residue was suspended in 400 ml ethyl acetate and stirred for one hour. Salts were filtered and the ethyl acetate layer was concentrated under reduced pressure to get N-acetyl D-serine methyl ester as an oil (93.22 g, Yield: 90%, HPLC: 98.7%),

[α]$_D^{20}$=+12.7 (C=1.9 in MeOH); IR(KBr):3389, 2957, 1739, 1651, 1547, 1439, 1377, 1292, 1219, 1148, 1078, 982, 772, 672 Cm$^{-1}$; H$^1$NMR: (300 MHz, DMSO), δ1.86 (s, 3H), 3.55-3.70 (m, 5H), 4.29-4.35 (m, 1H), 5.04-5.07 (t, 1H), 8.20-8.23 (d, 1H); $^{13}$CNMR (300 MHz, DMSO) δ 22.19, 51.6, 54.6, 61.2, 169.4, 171.1.

Example-3

Preparation of (R)-2-Acetamido-N-Benzyl-3-Hydroxy-Propionamide

N-Acetyl-D-serine methyl ester (25 g, 0.155 mole) was dissolved in benzylamine (33.2 g, 0.3101 mole) at 0-5° C. The reaction mixture was allowed to room temperature and stirred for 12 hr. To the thick colorless precipitate formed was added 300 ml methyl tert-butyl ether and stirred for 6 hr. The product was filtered and dried under vacuum to obtain (R)-2-acetamido-N-benzyl-3-hydroxy-propionamide (30.0 g, Yield: 82%, HPLC: 98.9, Chiral HPLC: 96.2%).

M.P: 135-137° C., [α]$_D^{20}$=+16.4 (C=1 in MeOH), IR(KBr): 3323, 3269, 3192, 3087, 2960, 2931, 2845, 2889, 2502, 2091, 1952, 1638, 1559, 1498, 1455, 1431, 1379, 1297, 1249, 1217, 1154, 1070, 1054, 1042, 1025, 969, 928, 907, 888, 755, 731, 698, 660, 635, 604, 534, 467, Cm$^{-1}$; H$^1$NMR: (300 MHz, DMSO), δ1.87 (s, 3H), 3.57-3.62 (d, 2H), 4.27-4.32 (d, 3H), 7.19-7.32 (m, 5H), 7.94-7.96 (d, 1H), 8.36-8.40 (t, 1H); $^{13}$CNMR: (300 MHz, DMSO), δ 22.6, 41.98, 55.37, 61.72, 126.56, 126.94, 128.12, 128.49, 128.58, 139.35, 169.44, 170.27

Example-4

Preparation of (R)-2-Acetamido-N-Benzyl-3-Hydroxy-Propionamide

N-Acetyl-D-serine methyl ester (1.0 g, 0.0062 mole) was dissolved in benzylamine (6.64 g, 0.062 mole) at 0-5° C. The reaction mixture was heated and stirred at 65° C. for 12 hr. The excess benzylamine was removed by distillation under vacuum at 90° C. to get a thick white solid. To this was added 10 ml of methyl tert-butyl ether and stirred for 2 hr at room temperature. The product was filtered and dried under vacuum to obtain (R)-2-acetamido-N-benzyl-3-hydroxy-propionamide (1.09 g, Yield 75%, HPLC: 92%, Chiral HPLC: 78%).

Example-5

Preparation of (R)-2-Acetamido-N-Benzyl-3-Hydroxy-Propionamide

N-Acetyl-D-serine methyl ester (25 g, 0.155 mole) was dissolved in benzylamine (33.2 g, 0.3101 mole) at 0-5° C. To this triethylamine (3.13 g, 0.031 mole) was added at 0-5° C. The reaction mixture was allowed to cool to room temperature and stirred for 12 hr. To the thick colorless precipitate formed 300 ml methyl tert-butyl ether was added and stirred for 6 hr. The product was filtered and dried under vacuum to obtain (R)-2-acetamido-N-benzyl-3-hydroxy-propionamide (34.03 g, Yield: 93%, HPLC: 98.9, Chiral HPLC: 98.8%)

Example-6

Preparation of (R)-2-Acetamido-N-Benzyl-3-Hydroxy-Propionamide

The experiment was carried out as described in Example-5, except that triethylamine was replaced with diisopropylethyl amine (4.0 g, 0.031 mole) to obtain (R)-2-acetamido-N-benzyl-3-hydroxy-propionamide. (22.6 g, Yield 62%, HPLC: 98.4, Chiral HPLC: 98.2%)

Example-7

Preparation of (R)-2-Acetamido-N-Benzyl-3-Hydroxy-Propionamide

The experiment was carried out as described in Example-5, except that triethylamine was replaced with N-methyl morpholine (3.13 g, 0.031 mole) to obtain (R)-2-acetamido-N-benzyl-3-hydroxy-propionamide. (27.8 g, Yield: 76%, HPLC: 98.6, Chiral HPLC: 98.4%)

Example-8

Preparation of (R)-2-Acetamido-N-Benzyl-3-Hydroxy-Propionamide

The experiment was carried out as described in Example-5, except that triethylamine was replaced with DABCO (3.47 g, 0.031 mole) to obtain (R)-2-acetamido-N-benzyl-3-hydroxy-propionamide. (21.5 g, Yield: 59%, HPLC: 98.1%, Chiral HPLC: 98.1%)

Example-9

Preparation of (R)-2-acetamido-N-benzyl-3-hydroxy-propionamide

The experiment was carried out as described in Example-5, except that triethylamine was replaced with DBU (4.7 g, 0.031 mole) to obtain (R)-2-acetamido-N-benzyl-3-hydroxy-propionamide. (25.9 g, Yield: 71%, HPLC: 98.3, Chiral HPLC: 98.2%)

Example-10

Preparation of (R)-2-Acetamido-N-Benzyl-3-Hydroxy-Propionamide

N-Acetyl-D-serine methyl ester (1.0 g, 0.0062 mole) was dissolved in benzylamine (1.32 g, 0.0124 mole) at 0-5° C. To this was added triethylamine (0.125 g, 0.00124 mole) at 0-5° C. The reaction mixture was heated and stirred at 60° C. for 12 hr, cooled to room temperature, 20 ml methyl tert-butyl ether added and stirred for 3 hr. The product was filtered and dried under vacuum to obtain (R)-2-acetamido-N-benzyl-3-hydroxy-propionamide. (1.0 g, Yield: 68.4%, HPLC:94.8%, Chiral HPLC: 81.2%), Example-11

Preparation of (R)-2-Acetamido-N-Benzyl-3-Hydroxy-Propionamide

The experiment was carried out as described in Example-10, but conducted at 40° C. instead of 60° C. to obtain (R)-2-acetamido-N-benzyl-3-hydroxy-propionamide. (1.2 g, Yield: 82%, HPLC: 97.7%, Chiral HPLC: 92.09%)

Example-12

Preparation of Lacosamide (R)-2-Acetamido-N-benzyl-3-hydroxypropionamide (25 g, 0.1059 mole) was suspended in 125 ml of acetonitrile at room temperature. To this was added aqueous sodium hydroxide solution (6.3 g in 15 ml, 0.158 mol) drop wise, followed by dimethyl sulfate (26.7 g, 0.211 mole) drop wise. The reaction mixture was stirred for one hour and concentrated under reduced pressure. The resulting residue was dissolved in 200 ml dichloromethane and the solution washed with water (100 ml×3). The organic layer was treated with 1 g charcoal and stirred for one hour. It was filtered and the filtrate was concentrated under reduced pressure. The solid residue obtained was dissolved in acetone and precipitated by adding diisopropyl ether to obtain Lacosamide. (18.5 g, Yield: 70%; chiral HPLC: 99.8% and chemical HPLC: 99.7%)

M.P: 144-146° C., $[\alpha]_D^{20}$=+15.8 (C=1 MeOH); IR (KBr): 3287, 3003, 2848, 1638, 1454, 1395, 1220, 1138, 945, 694, 605, 495. Cm$^{-1}$; H$^1$NMR: (300 MHz, CDCl$_3$), δ2.02 (s, 3H), 3.37 (s, 3H), 3.43-3.46 (dd, 1H), 3.77-3.82 (dd, 1H), 4.45-4.48 (d, 2H), 4.53-4.59 (m, 1H), 6.48-6.50 (d, 1H), 6.83 (s, 1H), 7.24-7.36 (m, 5H); $^{13}$CNMR: (300 MHz, CDCl$_3$), δ23.10, 43.50, 52.50, 59.04, 71.88, 127.43, 128.65, 137.91, 170.03, 170.40.

We claim:

1. A process for the preparation of Lacosamide having the formula (I):

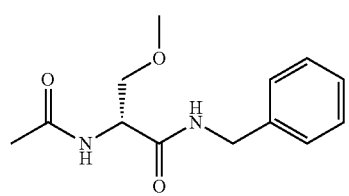

(I)

comprising the steps of:
(a) reacting N-acetyl-D-serine methyl ester of the formula (II),

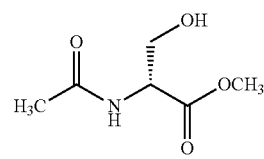

(II)

with benzylamine of formula (III)

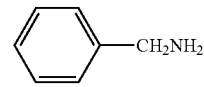

(III)

at a temperature below 40° C., in the presence of a non-nucleophilic base, to produce a benzyl amide derivative of the formula (IV) of enantiomeric purity higher than 95%; and

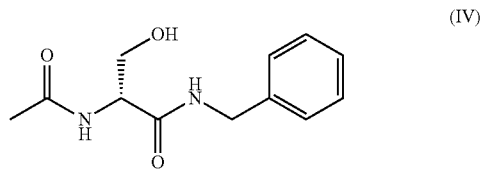 [SMILES: CC(=O)N[C@H](CO)C(=O)NCc1ccccc1] (IV)

(b) subjecting the benzyl amide of the formula (IV) obtained in step (a) to methylation reaction using dimethylsulfate in the presence of a base.

2. A process according to claim 1, wherein the non-nucleophilic base is selected from the group consisting of triethylamine, diisopropylethyl amine (DIPEA), N-methyl morpholine (NMM), 1,4-diazabicyclo-[2.2.2]octane (DABCO) and 1,8-diazabicyclo[5.4.0]undec-7-ene (DBU).

3. A process according to claim 2, wherein the non-nucleophilic base is triethylamine.

4. A process according to claim 1 step-a, wherein the reaction between (II) and benzylamine (III) is carried out at 25° C.

* * * * *